United States Patent [19]

Richter et al.

[11] 4,105,037

[45] Aug. 8, 1978

[54] RELEASABLE ELECTRICAL CONNECTING MEANS FOR THE ELECTRODE TERMINAL OF AN IMPLANTABLE ARTIFICIAL CARDIAC PACEMAKER

[75] Inventors: Gerolf Richter; Scott B. Shanks, both of Berlin, Fed. Rep. of Germany

[73] Assignee: Biotronik Mess- und Therapiegeräte GmbH & Co., Berlin, Fed. Rep. of Germany

[21] Appl. No.: 794,659

[22] Filed: May 6, 1977

[51] Int. Cl.² .............................................. A61N 1/36
[52] U.S. Cl. ................................................. 128/419 P
[58] Field of Search ........ 128/419 P, 419 PG, 419 PS

[56] References Cited

U.S. PATENT DOCUMENTS

| 3,649,367 | 3/1972 | Purdy | 128/419 P |
|---|---|---|---|
| 3,683,932 | 8/1972 | Cole | 128/419 P |
| 3,757,789 | 9/1973 | Shanker | 128/419 P |
| 3,760,332 | 9/1973 | Berkovits et al. | 128/419 P |
| 3,822,707 | 7/1974 | Adducci et al. | 128/419 PS |
| 3,867,950 | 2/1975 | Fischell | 128/419 PS |
| 3,871,382 | 3/1975 | Mann | 128/419 P |
| 3,920,888 | 11/1975 | Barr | 128/419 P |

*Primary Examiner*—William E. Kamm
*Attorney, Agent, or Firm*—Spencer & Kaye

[57] ABSTRACT

An implantable, artifical cardiac pacemaker including a releasable electrical connection composed of a plug and a mating receptacle provided with conical sealing surfaces for the connection of an electrode, the sealing surfaces contacting one another, once connection is made, in a manner to hermetically seal the connection as well as of the interior of the pacemaker housing against external influences, a ceramic ring serving to insulate the conductive pacemaker housing from the connection.

27 Claims, 4 Drawing Figures

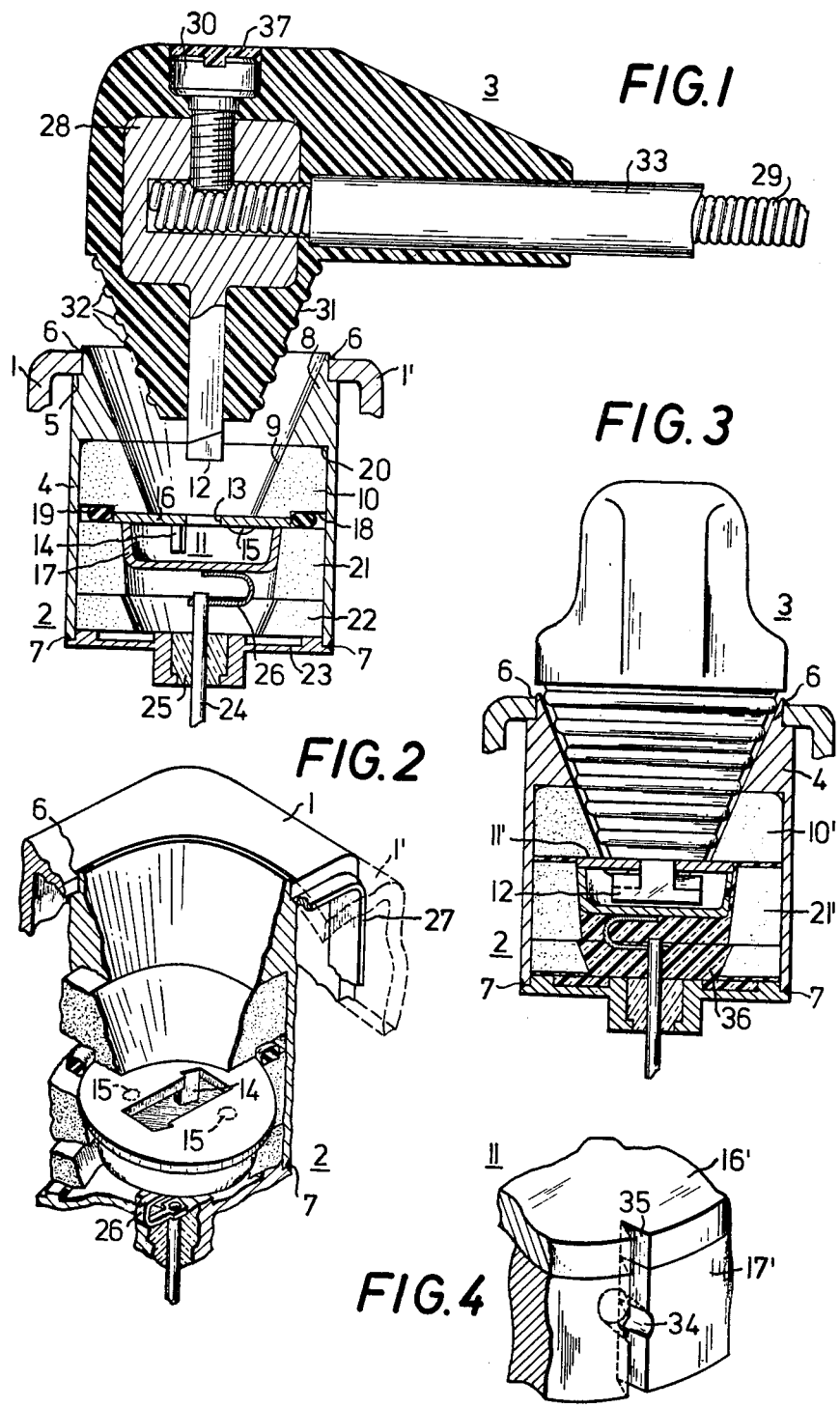

RELEASABLE ELECTRICAL CONNECTING MEANS FOR THE ELECTRODE TERMINAL OF AN IMPLANTABLE ARTIFICIAL CARDIAC PACEMAKER

BACKGROUND OF THE INVENTION

The present invention relates to releasable electrical connecting means for the connection of an electrode to an implantable artificial cardiac pacemaker.

In an artificial cardiac pacemaker it is necessary to electrically conductively connect the electrode which serves to transmit pulses from or to the heart to an input or output of the pacemaker circuit, and the connection itself must be electrically insulated with respect to the conductive material of the cardiac pacemaker housing. Moreover, the connection must not impair the fluid-tightness of the housing against attack by body fluids.

There already exist various screw-in or plug-in connections for connecting an electrode to a pacemaker but many of them have the drawback of not being sufficiently fluid-tight to protect the interior of the pacemaker against the penetration of body fluids over a period of many years. Other known connection devices do not have a sufficiently high resistance to corrosion.

In the case of pacemakers using batteries that permit continuous operation for periods of the order of 10 years or more, the connection device must satisfy even more stringent requirements relative to durability and ability to withstand the influences to which they will be subjected in the implanted state. These requirements in particular are not met by the presently known plug-in and screw-in connections.

In addition, in order to reduce the costs involved in the use of artificial cardiac pacemakers, it has been found desirable to make them reusable. It is possible, in principle, to reuse a pacemaker after it has been sterilized, i.e., to implant it in another patient. The prerequisite is, however, that the pacemaker housing be capable of being sterilized in such a manner as to remove all contaminants which may be damaging to the new user. It seems that this requirement can be met only if the pacemaker does not contain any parts made of an epoxide material which may come into contact with the body of the patient, or at least if the surface of the epoxide material exposed to body fluids is minimal. However, most of the known electrode connecting means include components which have large exposed surfaces of epoxide material and this limits reuse of the pacemaker.

In other types of implantable artificial cardiac pacemakers, the contact element which is attached to the pacemaker housing in order to connect an external electrode is rigidly connected with a sealing and insulating passage through the housing. If this contact element is subjected to mechanical stresses, or if the plug for the electrode is removed, there then exists the danger of tearing of the sealing element and the hermetic seal of the pacemaker is no longer assured.

SUMMARY OF THE INVENTION

It is a primary object of the present invention to overcome the above-noted drawbacks and difficulties.

A more specific object of the present invention is to provide an improved releasable electrical connection which produces secure attachment of an electrode to an implantable artificial cardiac pacemaker as well as good electrical contact.

A still further object of the invention is to assure that the electrical connection is permanently insulated against the housing potential and thus against the potential of the surrounding body tissues, thereby to reliably prevent creation of parasitic current leakage paths.

These and other objects of the invention are achieved by provision of a novel releasable connector assembly for use in an implantable cardiac pacemaker system including an electrode, an electrode housing within which one end of the electrode is secured, a pacemaker unit, and a pacemaker housing of electrically conductive material in which the pacemaker unit is secured, which connector assembly is composed of a first member secured to the pacemaker housing and including a first electrical connector element arranged to be connected to the pacemaker unit, a second member secured to the electrode housing and including a second electrical connector element in conductive contact with the one electrode end and arranged to be placed in conductive contact with the first connector element, one of the members defining a recessed conical surface located between the housing and connector element associated with the one of the members, the other of the members defining a protruding conical surface formed to establish a hermetic sealing connection with the recessed conical surface and located between the housing and connector element associated with the other one of the members, and the one of the members including a body of ceramic material disposed near the connector element associated with the one member and defining part of the recessed conical surface, and securing components associated with the members for releasably connecting them together with the conical surfaces in sealing contact and the first and second connector elements in conductive contact.

According to preferred embodiments of the invention, one of the electrical connector elements is in the form of a receptacle provided with an electrical lead and the other electrical connector element is in the form of a plug constructed to mate with said receptacle. In addition, according to preferred embodiments of the invention, the receptacle is included in the one member and the plug is included in the other member. Further, it is preferable for the one member to be associated with the pacemaker housing and the other member with the electrode housing.

A particular advantage of the invention is that the elements for sealing off the interior of the pacemaker housing are combined in a favorable manner with the elements for electrically insulating the connectors from the conductive outer housing of the pacemaker. The sealing elements in the form of mating conical surfaces prevent the penetration of body fluids to the region of the connectors and thus improve the effectiveness of the electrical insulation by preventing the formation of current leakage paths. The conical surfaces simultaneously serve to mechanically secure the connection between the connectors. The actual electrical insulation between that connection and the pacemaker housing is effected by the ceramic ring which forms part of the recessed conical surface and thus also constitutes a sealing element.

The occurrence of leakage paths for the electrical current between the conductive outer housing of the pacemaker and the connectors would lead to more rapid discharging of the energy source of the pacemaker. But the subsequent malfunction will not occur suddenly so that there is no immediate danger for the patient. The situation is different if body fluids penetrate into the interior of the pacemaker housing and there create damage which results in a sudden cessation of operation. Such operational malfunction must therefore be avoided under all circumstances. For that reason, the present invention provides further means to additionally seal off the interior of the pacemaker and to simultaneously provide an electrical path for connection to the electrical circuit of the pacemaker in the interior of the housing. The invention thus provides a "series connection", or successive arrangement, of a plurality of seals to seal the housing interior in a manner which affords a particularly high degree of security.

It is a further advantage of the present invention that the connecting structure possesses a high resistance to aging and to other damaging influences from body fluids. The connection can be easily disconnected even after the assembly has remained in a patient's body for more than 10 years, particularly since there are no screw connections between the connectors.

According to a further feature of preferred embodiments of the invention, mechanical stresses occurring during connection and disconnection of the connecting elements will not be transferred to the sealing members. The connecting structure according to the invention is easy to manufacture and install.

In further accordance with the present invention, an additional seal for the interior of the pacemaker is provided by filling the space between the contact elements and the sealed electrical passage to the interior of the pacemaker housing with a further sealing member having an epoxy resin base. This sealing member forms a third, additional obstacle in the "series connection" of the seals. The surfaces which it presents to penetrating body fluids are very small since, firstly, the body fluids coming from the outside can reach it only through a first sealing member and, secondly, it is only in the form of a filling mass, i.e. it can come in contact with body fluids only at minute cracks which are not covered by the other, solid, sealing members.

It is a further object of the invention to protect the interior of the pacemaker housing from damaging influences during welding of the assembly with electron beams.

This is accomplished, according to the invention, by the provision of a peripheral metallic extension of the member connected to the pacemaker housing. This extension is disposed between the interior of the pacemaker housing and a seam to be welded and has a thickness which is sufficient to reduce to a harmless level the damaging influences of the welding process at the interior of the housing. In the region of the other seams to be welded in the housing, there is provided in the housing interior an additional strip of metal which is of sufficient thickness and is suitable to reduce to a harmless level the damaging influences during welding at the interior of the housing.

BRIEF DESCRIPTION OF THE DRAWINGS

FIG. 1 is an elevational, cross-sectional view of a preferred embodiment of a connecting assembly according to the invention in the disconnected state.

FIG. 2 is a cut-away, perspective, detail view of the member of the connecting assembly of FIG. 1 which is connected to the pacemaker.

FIG. 3 is an elevation view showing a modified version of the electrical connecting assembly of FIG. 1 in the connected state, the components with the pacemaker being shown in cross section.

FIG. 4 is an enlarged detail view of a portion of the assembly of FIG. 3.

DESCRIPTION OF THE PREFERRED EMBODIMENTS

The electrical connector assembly shown in FIGS. 1 and 2 includes a receptacle member 2 permanently installed in a cardiac pacemaker housing, shown only in part and composed of two housing halves 1 and 1'. The assembly further includes a plug member 3 which is shown as being disconnected from the receptacle and in the relative orientation it must have for insertion into, or withdrawal from, receptacle member 2. Plug member 3 is connected with the receptacle member 2 before the pacemaker is implanted and both parts remain in this connected state during the period of operation of the pacemaker in the body of the patient.

The receptacle member 2 includes a sleeve 4 which is cylindrical. Like housing 1, 1' and all other metal parts of the assembly, receptacle 2 is made of a cobalt alloy which is substantially resistant to attach by body fluids. The technical identification of this alloy is MP 35 N and its use and properties are described in "J. Biomed. Mater. Res. Symposium, No. 5 (Part 1), pages 219–226 (1974)".

All other materials of the assembly have been selected to be compatible with the cobalt alloy so that no chemical stress potentials or mutually adverse influences on the materials are created.

The sleeve 4 is inserted between the two housing halves 1 and 1' of the pacemaker before the latter are connected together and is welded to the housing by electron beam welding. In order to provide a full penetration weld, the circumference of sleeve 4 is provided with a continuous shoulder 5, on which rests the housing 1, 1'. Connecting weld seams are identified as 6 and 7. A provision to protect the interior of the housing during electron beam welding is described below with reference to FIG. 2.

The sleeve 4 is substantially hollow in order to accommodate insulating and contact components. At the end of sleeve 4, which, in the installed state, faces the plug 3, a conical extension 8 is provided which forms part of a sealing surface 9. The conical extension 8 is followed by a first ceramic ring 10 which is inserted into the sleeve 4 and whose interior surface forms a part of sealing surface 9. Surface 9 has the geometrical shape of the superfices of a conical frustum and serves as the countersurface for a corresponding surface on plug 3, which will be described below.

This sealing surface 9 is the major contributor to the hermetic seal for the electrical connection and indirectly also to the sealing of the interior of the pacemaker housing against the influences if body tissues and fluids which surround the pacemaker in the implanted state.

The first ceramic ring 10 is made of a ceramic insulating material of the type used in the electrical arts. It is of such a thickness that safe electrical insulation between that part of sealing surface 9 which is part of sleeve 4 and the connecting element disposed at the other end of the thus formed funnel is assured. A thickness of substantially 4 mm will produce good results. This contact element is formed by an insert 11 to accommodate a plug-in contact. The first ceramic ring 10 prevents the formation of current leakage paths of any type which would constitute an additional load resistance for the reception and emission of signals and would decrease the amplitude of the received signals or the efficiency of the pacemaker, respectively. Such leakage paths would also result in increased loads on the energy source of the pacemaker and would thus considerably reduce its lifetime. The ceramic rings 10, 21 and 22 are $Al_2O_3$ 99.99 percent.

Insert 11 to accommodate a plug member constitutes a bayonet mount and forms the counterpiece for a T-shaped connecting element extension 12 on plug member 3. For this purpose, insert 11 is provided, as shown most clearly in FIG. 2, with an elongate opening 13 which is adapted, i.e. at least equal, to the size of contact extension 12. An abutment 14 and a detent knob 15 are provided along each side of opening 13. Connection is established by inserting extension 12 through opening 13 and rotating plug member 3 about a vertical axis in the plane of FIG. 1. Each leg of extension 12 slides over and past a respective knob 15 and is stopped by a respective abutment 14. The knob 15 on each side serves to retain a respective leg of extension, i.e. to prevent unintentional rotation of plug member 3, after connection has been effected. Insert 11 includes a planar portion 16 having the opening 13 and a trough, or cup-shaped, portion 17 joined therewith. The connection between portions 16 and 17 can also be made by electron beam welding.

The resulting compact, closed design can be achieved in other ways by combinations of two molded pieces, so that those skilled in the art need not be limited to the illustrated embodiment. It is important that insert 11 have contact surfaces which permit easy installation and which assure that it will remain in a defined position and will remain sufficiently insulated and protected against leakage currents during and after installation, as will be explained in detail below.

Insert 11 is in sealing contact with the first ceramic ring 10 in the region of one planar surface of its flat part 16. The outer edge of this flat part 16 is flush with the inner edge of a recess 18 formed in the outer portion of the surface of ceramic ring 10 which faces part 16. A ring 19 of resilient, elastic material is inserted into the thus produced cavity. This ring is intended primarily to seal the cavity between ceramic ring 10 and ceramic ring 21. The individual parts can easily be inserted, one after the other, during assembly, from the end of the sleeve remote from the conical extension 8 and they will at once take up their final position while maintaining their proper spacings.

After ceramic ring 10 has been inserted, elastic ring 19 is inserted into recess 18. This ring fixes insert 11, which follows ceramic ring 10, in its proper position until insert 11 is finally fixed in its position by a further ceramic ring 21 which is the next piece to be installed.

By this procedure it is very easy to assemble the various parts in a manner such that, in the assembled state, all of the individual parts are positioned with the proper and sealing fit since the individual parts are each sealingly supported on one another via planar surfaces. Moreover, insert 11 is arranged at a sufficient distance from sleeve 4 so that good insulation is assured.

The second ceramic ring 21 is followed by yet a third ceramic ring 22 which partly fills the remaining space up to a cover piece 23. Cover piece 23 has a passage containing an electrical lead 24 embedded in an insulation body 25 of glass material constituting an additional hermetic seal protecting the interior of the pacemaker housing against the penetration of body fluids. A weld between cover member 23 and a sleeve 4 and the insulation 25 in the passage of member 23 provide a hermetic seal for receptacle 2. In order to prevent mechanical stresses on lead 24 which might lead to a crack in the glass insulation 25, lead 24 is connected to trough portion 17 of insert 11 via a resilient strip 26 which is fastened at its ends by spot welding.

In FIG. 2 the structure of the receptacle member is shown in a perspective view. It can be seen that the T-shaped contact extension 12 of plug member 3 must be inserted from the top into the elongate opening 13 of insert 11. Then clockwise rotation of the plug member, looking down from above the assembly, moves the T-shaped extension 12 over and past knobs 15 until it is halted by abutments 14 and the plug member is then held in this locked condition.

For reasons of clarity the resilient strip 26 is shown in FIG. 2 rotated by 90° with respect to the showing in the other figures. Moreover, in FIG. 2, housing half 1' is shown in broken lines.

At the point of connection between the two housing halves, a radiation or energy shield 27 is additionally provided behind the weld seam to shield the interior of the housing against damaging influences of the electron beam welding process when the housing halves are being connected. Such damaging influences may be generated by the impingement of electrons in the welding region. This includes X and gamma rays as well as discharged electrons. The free radicals produced by the discharge of electrons are particularly damaging of the corrosion effects which they indirectly produce in the interior of the pacemaker housing.

Radiation shield 27 has the form of a metal band encircling the seam of the two housing halves and it has a thickness which is sufficient to suppress to a sufficient degree penetration of damaging radiation into the interior of the pacemaker housing.

No radiation shield is provided in the regions of weld seams 6 since the wall thickness of sleeve 4 itself shields the interior of the pacemaker housing from the impinging radiation. For this purpose the continuous shoulder 5 is designed in the region of the weld connection between housing 1, 1' and sleeve 4 so that a layer of metallic material of sufficient thickness is disposed between weld seam 6 and the interior of the pacemaker housing to reduce the radiation entering during welding to a harmless level.

The plug member 3 shown in FIG. 1 includes a machined metal insert 28 which ends in the plug element with its T-shaped contact extension 12. The upper edges of the legs of the T-shaped contact extension 12 are inclined relative to a plane normal to the plug element length, as shown in the drawing, in order to facilitate sliding over knobs 15 of the receptacle. The metal insert 28 has an opening to accommodate the end of the helical conductor of the electrode lead. The latter is secured by a screw 30, which is sealed by a silicone medical adhesive 37.

During production of plug member 3, the metal insert 28 is encased in a silicone material by molding, thus simultaneously producing the electrode housing and the conical surface 31 which is part of the plug member and which is adapted to mate with the sealing surface 9 of the receptacle. The conical surface 31 is additionally provided with molded sealing strips, or bands, 32 which have the form of rings surrounding the conical surface 31. The insulation 33 of the electrode lead is made of rubber and is embedded in the molded housing of plug member 3.

In the operational state of the pacemaker, the plug member 3 takes on the position shown in FIG. 3. Sealing rings 32 are pressed firmly against sealing surface 9 of the receptacle member and form a permanent barrier to the penetration of body fluids in the direction toward the connecting elements, forming a "Lambrath seal". At the same time, rings 32 have the effect of a spring and act to press the T-shaped contact extension 12 against the underside of flat member 16 of insert 11 and in this way permit permanent contacting. Plug member 3 and receptacle member 2 constitute a simple two-part plug-in connecting structure which can easily be disconnected without the need for tools, and in particular even after several years. The connecting elements are optimally protected against the formation of leakage paths for electrical current due to penetration by body fluids.

The embodiment according to the invention shown in FIG. 3 differs from that of FIGS. 1 and 2 in that the cavities remaining under insert 11' to accommodate the lead and between the first and second ceramic rings 10' and 21' are filled with an epoxide material 36. The sealing ring 19 of the embodiment of FIGS. 1 and 2 is here eliminated. The shape of ceramic rings 10' and 21' has been adapted accordingly. Recess 18 can also be eliminated from ring 10'.

In order to be able to introduce the epoxide material after assembly of receptacle member 2, a bore 34 and a notch 35 in the region of this bore are provided in cup-shaped member 17' and flat member 16' of insert 11', as can be seen in the enlarged detail view of FIG. 4. The epoxide material can be injected through this bore from the interior of insert 11', by vacuum potting. If flows from bore 34 into notch 35, the space enclosed by rings 21' and 22, recesses in cover member 23, and into the annular cavity between the first and second ceramic ring 10' and 21'. The region around insert 11' and thus the entire cross section of the opening provided for installation of receptacle member 2 in the pacemaker housing, it thus additionally sealed off hermetically.

Since the epoxy resin can come in contact with the body fluids against which the interior of the pacemaker must be protected only in the areas of minute cracks, the danger of the body fluids attacking this epoxy resin, and thus the danger that the pacemaker would be "contaminated" for a second implant in another patient, is reduced to a negligible minimum. The epoxy resin may be manufactured by Hysol Inc. No. C8-W795 and hardener H-W796 mixed in a ratio 4:1.

The use of adapted, aging resistant and body compatible materials assures maintenance of the positive properties of the plug-in connection over a period of time which exceeds the design lifetime of the pacemaker with great certainty. A series of modifications is conceivable, in addition to the described advantageous embodiments of the invention, which are obvious for the person skilled in the art and which lie within the scope of the present invention. For example, it would also be advantageous to design the conical surface in the plug-in member as a smooth surface, in which case the selection of material, the intended use and the available tools play a part. The described contact means may also be replaced by others having a similar effect and the operation of plug-in member and receptacle member may be designed differently. It is conceivable, for example, to completely or partially interchange the receptacle and the plug-in member with respect to their association with the pacemaker housing and the electrode housing. The silicone material used in the plug-in member may be Dow Corning Medical Silicone Type A.

It will be understood that the above description of the present invention is susceptible to various modifications, changes and adaptations, and the same are intended to be comprehended within the meaning and range of equivalents of the appended claims.

What is claimed is:

1. A releasable connector assembly for use in an implantable cardiac pacemaker system including an electrode, an electrode housing within which one end of the electrode is secured, a pacemaker unit, and a pacemaker housing of electrically conductive material in which the pacemaker unit is secured, said connector assembly comprising: a first member secured to the pacemaker housing and including first electrical connector means arranged to be connected to the pacemaker unit; a second member secured to the electrode housing and including second electrical connector means in conductive contact with the one electrode end and arranged to be placed in conductive contact with said first connector means; one of said members defining a recessed conical surface located between the housing and connector means associated with said one of said members, the other of said members defining a protruding conical surface formed to establish a hermetic sealing connection with said recessed conical surface and located between the housing and connector means associated with said other one of said members, and said one of said members including a body of ceramic material disposed near said connector means associated with said one member and defining part of said recessed conical surface; and securing means associated with said members for releasably connecting them together with said conical surfaces in sealing contact and said first and second connector means in conductive contact.

2. An arrangement as defined in claim 1 wherein one of said electrical connector means is in the form of a receptacle provided with an electrical lead and the other of said electrical connector means is in the form of a plug constructed to mate with said receptacle.

3. An arrangement as defined in claim 2 wherein said one of said electrical connector means is included in said one member and said other of said electrical connector means is included in said other member.

4. An arrangement as defined in claim 3 wherein said first and second connector means are made of the same conductive material as the pacemaker housing.

5. An arrangement as defined in claim 4 wherein the conductive material is a cobalt alloy.

6. An arrangement as defined in claim 2 wherein said body of ceramic material has a thickness of substantially four millimeters in the direction between the housing and connector means associated with said one of said members.

7. An arrangement as defined in claim 2 wherein said one of said members is said first member and said first member has a portion which defines a part of said recessed conical surface remote from said first connector means and made of the same conductive material as the pacemaker housing.

8. An arrangement as defined in claim 1 wherein the pacemaker housing and said first member connected therewith are welded together.

9. An arrangement as defined in claim 1 wherein one of said conical surfaces is provided with transverse, circumferential ribs of an elastic material.

10. An arrangement as defined in claim 1 wherein said securing means comprise components secured to each of said members to define a bayonet-like connection between said members.

11. An arrangement as defined in claim 10 wherein said components of said securing means simultaneously form parts of said first and second connector means.

12. An arrangement as defined in claim 1 wherein said one of said members is said first member and said other one of said members is said second member.

13. An arrangement as defined in claim 12 wherein said first electrical connector means is in the form of a receptacle and said second electrical connector means is in the form of a plug constructed to mate with said receptacle.

14. An arrangement as defined in claim 13 wherein said recessed conical surface constitutes an opening for said receptacle.

15. An arrangement as defined in claim 13 wherein said first member comprises a sleeve presenting an extension defining part of said conical surface and said body of ceramic material is in the form of a ring inserted into said sleeve.

16. An arrangement as defined in claim 15 wherein said receptacle is constituted by a unit inserted into said sleeve adjacent said ring of ceramic material.

17. An arrangement as defined in claim 16 wherein said ring of ceramic material substantially covers said receptacle.

18. An arrangement as defined in claim 16 wherein said first member comprises at least one further ring of ceramic material inserted into said sleeve, and a closing cover closing the end of said sleeve remote from said recessed conical surface, said further ring being disposed between said receptacle and said closing cover.

19. An arrangement as defined in claim 18 wherein said closing cover is provided with a passage and said first member further comprise an electrically insulated conductive lead extending through said passage, and electrically conductive, resilient spring means disposed in said sleeve and conductively connecting said receptacle to said lead.

20. An arrangement as defined in claim 19 wherein said cover is provided with an insulating body of glass filling said passage and holding said lead.

21. An arrangement as defined in claim 16 wherein: said ring of ceramic material has an axial end face facing said receptacle and provided with a circumferential recess adjacent its outer periphery, said recess being inwardly delimited by a circumferential edge; said receptacle is constructed to have an outer periphery aligned with said circumferential edge; and said first member additionally comprises a sealing ring of resilient material located in said recess and enclosing said circumferential edge and said outer periphery of said receptacle.

22. An arrangement as defined in claim 16 wherein said receptacle is spaced inwardly from said sleeve and further comprising a mass of plastic sealing material filling the space remaining between said receptacle and said sleeve.

23. An arrangement as defined in claim 22 wherein said receptacle is provided with a fill opening for injection of the plastic sealing material from the side of said receptacle which in the assembled state of said first member is accessible from the exterior of the pacemaker housing.

24. An arrangement as defined in claim 13 wherein said second member defining said protruding conical surface and said electrode housing are constituted by a one-piece molded body of flexible plastic material.

25. An arrangement as defined in claim 24 wherein said molded body further includes integral ribs extending circumferentially around said protruding conical surface.

26. An arrangement as defined in claim 1 wherein said first member is secured to the pacemaker housing by a seam formed by electron beam welding, and said first member is provided with a circumferential shoulder interposed between said seam and the interior of the pacemaker housing for reducing to a harmless level damaging influences at the interior of the pacemaker housing due to the welding of the seam.

27. An arrangement as defined in claim 1 wherein the pacemaker housing is composed of two parts welded together along a seam, and further comprising a metal strip attached to the inside of the pacemaker housing in the region of said seam and having a thickness sufficient to reduce to a harmless level damaging influences at the interior of the pacemaker housing due to the welding of the seam.

* * * * *